(12) United States Patent
Kano et al.

(10) Patent No.: US 10,160,982 B2
(45) Date of Patent: Dec. 25, 2018

(54) METHOD FOR PRODUCING ACRYLAMIDE

(71) Applicant: Mitsubishi Chemical Corporation, Tokyo (JP)

(72) Inventors: Makoto Kano, Kanagawa (JP); Kozo Murao, Kanagawa (JP)

(73) Assignee: Mitsubishi Chemical Corporation, Tokyo (JP)

( * ) Notice: Subject to any disclaimer, the term of this patent is extended or adjusted under 35 U.S.C. 154(b) by 0 days.

(21) Appl. No.: 14/650,063

(22) PCT Filed: Nov. 15, 2013

(86) PCT No.: PCT/JP2013/006713
§ 371 (c)(1),
(2) Date: Jun. 5, 2015

(87) PCT Pub. No.: WO2014/091676
PCT Pub. Date: Jun. 19, 2014

(65) Prior Publication Data
US 2015/0315620 A1    Nov. 5, 2015

(30) Foreign Application Priority Data

Dec. 10, 2012   (JP) .................................. 2012-269131

(51) Int. Cl.
*C12P 13/02*    (2006.01)
(52) U.S. Cl.
CPC ................................... *C12P 13/02* (2013.01)
(58) Field of Classification Search
CPC ............................... C12P 13/02; C07C 231/24
See application file for complete search history.

(56) References Cited

U.S. PATENT DOCUMENTS

| | | | |
|---|---|---|---|
| 4,555,487 A | 11/1985 | Yamada et al. | |
| 6,043,061 A | 3/2000 | Ishii et al. | |
| 9,057,084 B2 | 6/2015 | Kanou et al. | |
| 9,102,590 B2 | 8/2015 | Kanou et al. | |
| 2002/0160466 A1 | 10/2002 | Abe et al. | |
| 2004/0048348 A1 | 3/2004 | Murao et al. | |
| 2004/0175809 A1 | 9/2004 | Peterson et al. | |
| 2005/0064564 A1 | 3/2005 | Petersen et al. | |
| 2009/0171051 A1* | 7/2009 | Shibamoto ............ | C07C 231/06 526/303.1 |
| 2011/0171701 A1 | 7/2011 | Kano et al. | |
| 2012/0276601 A1* | 11/2012 | Kariya .................. | C12M 29/06 435/129 |
| 2014/0134683 A1* | 5/2014 | Kanou ................... | C12P 13/02 435/129 |

FOREIGN PATENT DOCUMENTS

| | | |
|---|---|---|
| CN | 102171357 A | 8/2011 |
| CN | 102286560 A | 12/2011 |
| EP | 1 182 260 A1 | 2/2002 |
| EP | 2 518 154 A1 | 10/2012 |
| EP | 2 716 765 A1 | 4/2014 |
| JP | 60 83581 | 5/1985 |
| JP | 2001 340091 | 12/2001 |
| JP | 2004 524047 | 8/2004 |
| JP | 2004 528037 | 9/2004 |
| KR | 1999-0037315 A | 5/1999 |
| KR | 2002-0020898 A | 3/2002 |
| SU | 1609444 A3 | 11/1990 |
| WO | 01 73101 | 10/2001 |
| WO | 02 50297 | 6/2002 |
| WO | WO 02/088373 A1 | 11/2002 |
| WO | 2010 038832 | 4/2010 |
| WO | 2012 039407 | 3/2012 |
| WO | WO 2012/165415 A1 | 12/2012 |

OTHER PUBLICATIONS

Zheng et al. Huaxue Yanjiu Yu Yingyong (2004)16(1): 37-39; abstract only.*
Nagasawa et al. Appl. Microbiol. Biotechnol. (1993) 40: 189-195 (Year: 1993).*
Extended European Search Report dated Oct. 27, 2015 in Patent Application No. 13863015.7.
International Search Report dated Jan. 21, 2014 in PCT/JP13/006713 filed Nov. 15, 2013.
Webster, N. A., et al., "Comparative characterisation of two *Rhodococcus* species as potential biocatalysts for ammonium acrylate production", Biotechnology Letters, vol. 23, No. 2, pp. 95-101, 2001.
Office Action dated Sep. 13, 2016 in Korean Patent Application No. 10-2015-7009207 (with English translation).
Office Action dated Oct. 25, 2016 in Russian Patent Application No. 2015127779 (with English language translation).
Office Action dated Apr. 4, 2018, in corresponding Chinese Patent Application No. 201380062946.4, with English translation of the first notice of opinion.

* cited by examiner

*Primary Examiner* — Susan Marie Hanley
(74) *Attorney, Agent, or Firm* — Oblon, McClelland, Maier & Neustadt, L.L.P.

(57) ABSTRACT

Provided is a method that is for producing acrylamide, continuously produces acrylamide from acrylonitrile using a biocatalyst, and is characterized in that a continuous reaction is started by means of introducing acrylamide into a reaction vessel and then causing acrylonitrile to contact a biocatalyst. The method for producing acrylamide has superior operability and a low cost, and is capable of continuously extracting an aqueous solution of acrylamide at a target concentration in a short period of time after starting the continuous reaction.

14 Claims, No Drawings

METHOD FOR PRODUCING ACRYLAMIDE

FIELD OF THE INVENTION

The present invention relates to a method for producing acrylamide, more specifically to a method for producing acrylamide from acrylonitrile using a biocatalyst.

BACKGROUND ART

Producing a desired compound using a biocatalyst has benefits such as mild reaction conditions, a higher purity level of the reaction product with fewer byproducts contained therein, and simplified production procedures. Accordingly, such a method is used for producing various compounds. To produce amide compounds, biocatalysts have been widely used since the discovery of nitrile hydratase, which is an enzyme to convert a nitrile compound to a corresponding amide compound.

As for industrially producing acrylamide using a biocatalyst, a so-called continuous reaction method is widely known; namely, while raw materials and a biocatalyst are introduced into a reaction vessel continuously or intermittently, a solution of the produced acrylamide is continuously or intermittently retrieved from the vessel. Examples of continuous reactions are described in patent publications 1~4.

In a known method for continuously producing acrylamide, water is introduced into a reaction vessel in advance of initiating continuous reactions. Patent publications 1 and 2 describe methods for introducing water into a reaction vessel in advance of initiating continuous reactions. Also, in patent publications 3 and 4, after water and a biocatalyst are introduced in advance of initiating continuous reactions and are then heated to a predetermined temperature, acrylonitrile is supplied into the reaction vessel to initiate continuous reactions.

PRIOR ART PUBLICATION

Patent Publication

Patent publication 1: JP2001-340091A
Patent publication 2: WO2012/039407
Patent publication 3: JP2004-524047A
Patent publication 4: JP2004-528037A

SUMMARY OF THE INVENTION

Problems to be Solved by the Invention

After initiating continuous reactions, it takes a while for the concentration of an acrylamide solution retrieved from the vessel to reach the desired level. The produced acrylamide is diluted by water that was introduced into the reaction vessel beforehand in each of the aforementioned patent publications 1~4. Accordingly, the concentration of the acrylamide solution retrieved from the vessel remains lower than the desired level for some time after continuous reactions are initiated.

The acrylamide solution with a lower concentration than the desired concentration level cannot serve as a finished product. Thus, it is necessary to concentrate the solution to a desired level or to recycle the solution by retrieving it from the reaction vessel and feeding it back to the vessel. As a result, the cost of equipping devices necessary for concentration or recycling purposes, along with energy costs, increases. In addition, operational procedures will be complex.

Considering the above, the objective of the present invention is to provide a method for continuously producing acrylamide from acrylonitrile using a biocatalyst; namely, to provide a method for producing acrylamide at low cost with simplified procedures, which enables an acrylamide solution with a desired concentration level to be continuously retrieved from shortly after continuous reactions are initiated.

Solutions to the Problems

To solve the aforementioned problems, in a method for continuously producing acrylamide from acrylonitrile using a biocatalyst, the present invention is characterized in that acrylamide is introduced into a reaction vessel, and then continuous reactions are initiated by bringing acrylonitrile into contact with the biocatalyst.

More specifically, one aspect of the present invention is to provide a production method in which continuous reactions are conducted in N number of reaction vessels ("N" is a whole number of 1 or greater) that are connected in series. Before initiating continuous reactions, the concentration of the acrylamide solution to be introduced into the i-th reaction vessel ("i" is a whole number of 1~N) is set at $C_i$ [mass %] or higher obtained by formula (1) shown below.

$$C_i = [(\Sigma X_n \times 1.34)/(\Sigma F1_n + \Sigma F2_n + \Sigma FX_n)] \times 100 - 10 \qquad \text{formula (1)}$$

(in the formula, $\Sigma X_n$ indicates the total flow rate [kg/hr] of an acrylonitrile solution to be supplied to the first through i-th reaction vessels;

$\Sigma F1_n$ indicates the total flow rate [kg/hr] of the raw water to be supplied to the first through i-th reaction vessels; and $\Sigma F2_n$ indicates the total flow rate [kg/hr] of the biocatalyst solution to be supplied to the first through i-th reaction vessels.)

In the production method, the concentration $C_i$ is preferred to be 5%~60%. In addition, acrylamide is preferred to be introduced into a reaction vessel into which an acrylonitrile solution is directly supplied. Moreover, the liquid amount of the acrylamide solution to be present in a reaction vessel prior to initiating continuous reactions is preferred to be 70%~120% of the liquid amount in the reaction vessel during continuous reactions. Also, prior to initiating continuous reactions, a reaction vessel is preferred to contain 3000~150000 U of a biocatalyst (activity at reaction temperature of 10° C.) per 1 liter of the liquid in the reaction vessel. The production method uses a continuous reaction vessel that is made up of 2~10 connected units, for example.

In the embodiments of the present invention, "a method for continuously producing acrylamide" means a continuous production method (continuous reactions) performed by continuously or intermittently supplying reaction materials (including biocatalyst, acrylonitrile and raw water); and by continuously or intermittently retrieving a reaction mixture (including the reaction materials and produced acrylamide) without retrieving the entire amount of the reaction mixture in the reaction vessel.

Effects of the Invention

According to one aspect of the present invention, an acrylamide solution having a desired concentration level is obtained shortly after the initiation of the continuous reactions, thereby enabling low-cost, efficient production of acrylamide.

DETAILED DESCRIPTION OF THE EMBODIMENTS

The following is a detailed description of a method for producing acrylamide according to the embodiments of the present invention.
[Biocatalyst]
Biocatalysts include animal cells, plant cells, organelles, bacterial cells (live cells or dead cells) and treated products thereof that contain enzymes to catalyze desired reactions. Examples of treated products are raw or purified enzymes extracted from cells, organelles or bacterial cells, as well as animal cells, plant cells, organelles, bacterial cells (live cells or dead cells) or enzymes themselves immobilized by using comprehensive methods, crosslinking methods, carrier-binding methods or the like.

Examples of animal cells include monkey cells COS-7, Vero cells, CHO cells, mouse L cells, rat GH3 cells, human FL cells and the like. Examples of plant cells include tobacco BY-2 cells.

Examples of bacterial cells are such microorganisms that belong to the genus *Nocardia*, the genus *Corynebacterium*, the genus *Bacillus*, the genus *Pseudomonas*, the genus *Micrococcus*, the genus *Rhodococcus*, the genus *Acinetobacter*, the genus *Xanthobacter*, the genus *Streptomyces*, the genus *Rhizobium*, the genus *Klebsiella*, the genus *Enterobacter*, the genus *Erwinia*, the genus *Aeromonas*, the genus *Citrobacter*, the genus *Achromobacter*, the genus *Agrobacterium*, the genus *Pseudonocardia* and the like.

Those animal cells, plant cells, organelles and bacterial cells include wild types and genetically modified types.

As for immobilization methods, a comprehensive method is to wrap bacterial cells or enzymes in a fine mesh of a polymer gel or to coat them with semipermeable polymer membranes; a crosslinking method is to crosslink enzymes using an agent having two or more functional groups (polyfunctional crosslinking agent); and a carrier-binding method is to bind enzymes to a water-insoluble carrier. Carriers to be used for immobilization are, for example, glass beads, silica gels, polyurethane, polyacrylamide, polyvinyl alcohols, carrageenan, alginic acids, agars, gelatins and the like.

Examples of enzymes are, for example, nitrile hydratases produced by the aforementioned microorganisms or the like.

The amount of a biocatalyst to be used is properly selected according to the type and form of the biocatalyst. For example, it is preferred that the activity of a biocatalyst to be introduced into the reaction vessel be adjusted to be approximately 50~500 U per 1 milligram of dry cells at a reaction temperature of 10° C. In the present application, a unit "U" means activity to produce 1 micromole/1 min. of acrylamide from acrylonitrile.
[Raw Water]
Raw water is used for hydration reactions with acrylonitrile when acrylamide is produced. Examples of raw water are water, solutions obtained by dissolving acid or salt in water and the like. Examples of acids are phosphoric acids, acetic acids, citric acids, boric acids, acrylic acids, formic acids and the like. Examples of salts are sodium salts, potassium salts, ammonium salts and the like of acids listed above. Specific examples of raw water are not particularly limited to any kind, but include pure water, ultrapure water and tap water; and buffers such as tris buffer, phosphate buffer, acetate buffer, citrate buffer and borate buffer. The pH (at 20° C.) of raw water is preferred to be 5~9.
[Acrylonitrile]
The type of acrylonitrile is not limited specifically, and any commercially available acrylonitrile may be used. To reduce the consumption of a biocatalyst when acrylamide is produced, acrylonitrile with a hydrocyanic acid concentration of 3 ppm or lower is preferred.

The reaction temperature (temperature of reaction mixture) for hydration reactions of acrylonitrile is not limited specifically, but is preferred to be 10~50° C., more preferably 15~40° C., and even more preferably 20~35° C. When the reaction temperature is 10° C. or higher, reaction activity of a biocatalyst is well enhanced. Also, when the reaction temperature is 50° C. or lower, inactivation of the biocatalyst is easier to suppress.
[Reaction Vessel]
One reaction vessel may be used, or multiple reaction vessels may be used in combination. However, when considering efficient operation in industrial mass production of acrylamide, using two or more reaction vessels, for example, 2~10 vessels, is preferred.

Examples of reaction vessels are stirred-tank, fixed-bed, fluidized-bed, moving-bed, columnar, and tubular reactors. Reaction vessels with different types may also be combined. A stirring device is preferred to be provided for the reaction vessel. Stirring blades are preferred as stirring device. The shape of stirring blades is not limited specifically, and paddles, disc turbines, propellers, helical ribbons, anchors, Pfaudler stirrers and the like may be used.

As for a reaction vessel into which raw water, a biocatalyst and acrylonitrile are supplied, it is not limited to the one positioned on the furthest upstream side, but may be any reaction vessel on the downstream side as long as reaction efficiency or the like is not lowered. Here, an upstream side means the side into which the reaction materials flow and a downstream side means the side from which the reaction mixture is retrieved.
[Additives]
To raw water or a reaction mixture (including reaction materials and the produced acrylamide), at least one type of water-soluble monocarboxylate having two or more carbon atoms may be added. Raw water containing at least one type of water-soluble monocarboxylate having two or more carbon atoms may also be supplied to a reaction vessel. Alternatively, when continuous reactions are conducted using multiple reaction vessels, at least one type of water-soluble monocarboxylate having two or more carbon atoms may be added to the reaction liquid containing acrylamide retrieved from a reaction vessel, and then the mixture may be supplied to the next reaction vessel. By so doing, the stability of acrylamide in the reaction liquid is improved.

A water-soluble monocarboxylate may be any saturated monocarboxylate or unsaturated monocarboxylate. Examples of saturated carboxylic acids are acetic acids, propionic acids, n-caproic acids and the like. Examples of unsaturated carboxylic acids are acrylic acids, methacrylic acids, vinylacetic acids and the like. Salts most likely to be used are sodium salts, potassium salts and ammonium salts of the saturated monocarboxylic acids or unsaturated monocarboxylic acids.

The amount of a water-soluble monocarboxylate to be added to acrylamide is preferred to be 20~5000 mg/kg in terms of acid.
[General Reaction Conditions]
The retention time for the reaction mixture (reaction time) is not limited specifically, but 1~30 hours, more preferably 2~20 hours, are preferred. Here, retention time indicates the value obtained when the total volume [m³] of reaction liquid (when there are multiple reaction vessels, the sum of the reaction mixture contained in all the reaction vessels) is divided by the flow rate [m³/hr] of the reaction mixture to be continuously retrieved from the reaction vessel.

To decrease the cooling load of a reaction vessel, raw water and/or acrylonitrile to be supplied are preferred to have a temperature of at least 5° C. lower than the reaction temperature. The pH for hydration reactions of acrylonitrile for producing acrylamide is preferred to be 6~9, more preferably 7~8.5. The pH values are measured, for example, using indicators, metal electrodes, glass electrodes, semiconductor sensors or the like. Among those, a glass electrode method widely used for industrial production is preferred.

[Initiation of Reaction]

The method for producing acrylamide according to the embodiment of the present invention is to continuously produce acrylamide from acrylonitrile by using a biocatalyst, characterized by bringing acrylonitrile into contact with a biocatalyst in the presence of acrylamide so as to initiate continuous reactions. More specifically, when acrylamide is present in a reaction vessel, reaction materials (including biocatalyst, acrylonitrile, raw water) are supplied to the reaction vessel to initiate continuous reactions. It is an option to introduce acrylamide first into a reaction vessel and to initiate reactions by adding reaction materials into the reaction vessel, or to simultaneously introduce acrylamide and reaction materials into a reaction vessel to initiate reactions. The state of acrylamide is not limited specifically, but a aqueous solution is preferred considering the ease of handling. When reactions are initiated in the presence of acrylamide, it is easier to retrieve an acrylamide solution with a desired concentration promptly after the reaction has started.

When multiple reaction vessels are used, acrylamide is introduced in advance into at least one reaction vessel prior to initiating continuous reactions. To retrieve an acrylamide solution with a desired concentration promptly after the reactions are initiated, acrylamide is preferred to be present in a reaction vessel into which acrylonitrile is directly supplied, or more preferably into all the reaction vessels, in advance of initiating continuous reactions.

After an acrylamide solution is introduced into a reaction vessel and before initiating continuous reactions, the temperature and/or the pH value of the acrylamide solution are preferred to be adjusted to the temperature and/or the pH value appropriate for continuous reactions.

[Concentration of Acrylamide Solution]

When multiple reaction vessels are used, the concentration of an acrylamide solution to be introduced into a reaction vessel prior to initiating continuous reactions is preferred to be adjusted separately for each reaction vessel. In particular, when N-number of reaction vessels ("N" is a whole number of 1 or greater) are connected in series to conduct continuous reactions, an acrylamide solution with a concentration of Ci [mass %] or higher, which is obtained by formula (1) below, is introduced into the i-th ("i" is a whole number of 1~N) reaction vessel prior to initiating continuous reactions. Here, when only one reaction vessel is used, it is also considered to be connected in series.

$$Ci=[(\Sigma X_n \times 1.34)/(\Sigma F1_n + \Sigma F2_n + \Sigma FX_n)] \times 100 - 10 \quad \text{formula (1)}$$

(in the formula, $\Sigma X_n$ indicates the total flow rate [kg/hr] of an acrylonitrile solution to be supplied to the first through i-th reaction vessels;

$\Sigma F1_n$ indicates the total flow rate [kg/hr] of the raw material water to be supplied to the first through i-th reaction vessels; and $\Sigma F2_n$ indicates the total flow rate [kg/hr] of the biocatalyst solution to be supplied to the first through i-th reaction vessels.)

Concentration $C_i$ indicates a concentration that is 10 mass % lower than the maximum acrylamide concentration in the reaction mixture in each reaction vessel when continuous reactions are in a steady phase.

If the concentration of an acrylamide solution to be introduced into a reaction vessel is lower than $C_i$ prior to initiating continuous reactions, it is hard to obtain an acrylamide solution with a desired concentration in a short period of time (within the aforementioned retention time, for example) after continuous reactions are initiated. Thus, the produced acrylamide solution itself cannot be used as a finished product, and further concentration or retrieval is required in a subsequent reaction process. As a result, an increase in cost causes disadvantages for industrial production.

On the other hand, the upper limit of the concentration of an acrylamide solution to be introduced into a reaction vessel prior to the initiation of continuous reactions is preferred to be ($C_i$+15) [mass %] or lower. If the concentration of an acrylamide solution to be introduced into a reaction vessel is higher than ($C_i$+15) [mass %], a process of diluting the acrylamide is required in a subsequent reaction process. Moreover, a high-concentration acrylamide solution is more likely to cause deterioration of the biocatalyst after continuous reactions are initiated, resulting in an increase in the amount of the biocatalyst, which in turn causes an increase in production cost.

To adjust the concentration of an acrylamide solution, it is an option to introduce into each reaction vessel an acrylamide solution having a concentration of $C_i$ mass % or higher, or to dilute an acrylamide solution or crystalline acrylamide in a reaction vessel by using raw water so as to set the concentration at $C_i$ mass % or higher.

[Specific Example of Concentration of Acrylamide Solution]

Concentration $C_i$ is preferred to be set at 5~60%. More preferably, concentration $C_i$ is set as follows depending on the number of reaction vessels.

(1) Number of Reaction Vessels (N) is One

By setting concentration $C_1$ at 20~40%, a desired acrylamide concentration of 25~34% is achieved in the reaction mixture continuously retrieved from the reaction vessel.

By setting concentration $C_1$ at 30~50%, a desired acrylamide concentration of 35~44% is achieved in the reaction mixture continuously retrieved from the reaction vessel.

By setting concentration $C_1$ at 40~60%, a desired acrylamide concentration of 45~55% is achieved in the reaction mixture continuously retrieved from the reaction vessel.

(2) Number of Reaction Vessels (N) is 2

By setting concentrations $C_1$ and $C_2$ in the first reaction vessel respectively positioned on the upstream side of the reaction and the second vessel positioned on its downstream side at 20~40% each, a desired acrylamide concentration of 25~34% is achieved in the reaction mixture continuously retrieved from the second reaction vessel.

Also, by setting concentrations $C_1$ and $C_2$ at 30~50% each, a desired acrylamide concentration of 35~44% is achieved in the reaction mixture continuously retrieved from the second reaction vessel.

Moreover, by setting concentrations $C_1$ and $C_2$ at 40~60% each, a desired acrylamide concentration of 45~55% is achieved in the reaction mixture continuously retrieved from the second reaction vessel.

(3) Number of Reaction Vessels (N) is 3

By setting concentration $C_1$ in the first reaction vessel positioned on the furthest upstream side of the reaction at 15~35%, and by setting concentrations $C_2$ and $C_3$ in the second and third reaction vessels positioned from the upstream side at 20~40% each, a desired acrylamide concentration of 25~34% is achieved in the reaction mixture continuously retrieved from the third reaction vessel.

Also, by setting concentration $C_1$ at 25~45%, and concentrations $C_2$ and $C_3$ at 30~50% each, a desired acrylamide concentration of 35~44% is achieved in the reaction mixture continuously retrieved from the third reaction vessel.

Moreover, by setting concentration $C_1$ at 35~55%, and concentrations $C_2$ and $C_3$ at 40~60% each, a desired acrylamide concentration of 45~55% is achieved in the reaction mixture continuously retrieved from the third reaction vessel.

(4) Number of Reaction Vessels (N) is 4

By setting concentration $C_1$ in the first reaction vessel positioned on the furthest upstream side of the reaction at 10~30%, and by setting concentrations $C_2$~$C_4$ in the second through fourth reaction vessels positioned from the upstream side at 20~40% each, a desired acrylamide concentration of 25~34% is achieved in the reaction mixture continuously retrieved from the fourth reaction vessel.

Also, by setting concentration $C_1$ at 20~40% and concentrations $C_2$~$C_4$ at 30~50% each, a desired acrylamide concentration of 35~44% is achieved in the reaction mixture continuously retrieved from the fourth reaction vessel.

Moreover, by setting concentration $C_1$ at 30~50% and concentrations $C_2$~$C_4$ at 40~60% each, a desired acrylamide concentration of 45~55% is achieved in the reaction mixture continuously retrieved from the fourth reaction vessel.

(5) Number of Reaction Vessels (N) is 5

By setting concentration $C_1$ in the first reaction vessel positioned on the furthest upstream side of the reaction at 10~30%, by setting concentration $C_2$ in the second reaction vessel positioned second from the upstream side at 15~35%, and by setting concentrations $C_3$~$C_5$ in the third through fifth reaction vessels at 20~40% each, a desired acrylamide concentration of 25~34% is achieved in the reaction mixture continuously retrieved from the fifth reaction vessel.

Also, by setting concentration $C_1$ at 15~30%, concentration $C_2$ at 25~45%, and concentrations $C_3$~$C_5$ at 30~50% each, a desired acrylamide concentration of 35~44% is achieved in the reaction mixture continuously retrieved from the fifth reaction vessel.

Moreover, by setting concentration $C_1$ at 25~45%, concentration $C_2$ at 35~55%, and concentrations $C_3$~$C_5$ at 40~60% each, a desired acrylamide concentration of 45~55% is achieved in the reaction mixture continuously retrieved from the fifth reaction vessel.

(6) Number of Reaction Vessels (N) is 6

By setting concentration $C_1$ in the first reaction vessel positioned on the furthest upstream side of the reaction at 5~25%, by setting concentration $C_2$ in the second reaction vessel positioned second from the upstream side at 10~30%, by setting concentration $C_3$ in the third reaction vessel at 15~35%, and by setting concentrations $C_4$~$C_6$ in the fourth through sixth reaction vessels at 20~40% each, a desired acrylamide concentration of 25~34% is achieved in the reaction mixture continuously retrieved from the sixth reaction vessel.

Also, by setting concentration $C_1$ at 10~30%, concentration $C_2$ at 20~40%, concentration $C_3$ at 25~45%, and concentrations $C_4$~$C_6$ at 30~50% each, a desired acrylamide concentration of 35~44% is achieved in the reaction mixture continuously retrieved from the sixth reaction vessel.

Moreover, by setting concentration $C_1$ at 20~40%, concentration $C_2$ at 30~50%, concentration $C_3$ at 35~55%, and concentrations $C_4$~$C_6$ at 40~60% each, a desired acrylamide concentration of 45~55% is achieved in the reaction mixture continuously retrieved from the sixth reaction vessel.

(7) Number of Reaction Vessels (N) is 7

By setting concentration $C_1$ in the first reaction vessel positioned on the furthest upstream side of the reaction at 5~20%, concentration $C_2$ in the second reaction vessel positioned second from the upstream side at 10~30%, concentration $C_3$ in the third reaction vessel at 15~35%, and by setting concentrations $C_4$~$C_7$ in the fourth through seventh reaction vessels at 20~40% each, a desired acrylamide concentration of 25~34% is achieved in the reaction mixture continuously retrieved from the seventh reaction vessel.

Also, by setting concentration $C_1$ at 10~30%, concentration $C_2$ at 20~40%, concentration $C_3$ at 25~45%, and concentrations $C_4$~$C_7$ at 30~50% each, a desired acrylamide concentration of 35~44% is achieved in the reaction mixture continuously retrieved from the seventh reaction vessel.

Moreover, by setting concentration $C_1$ at 15~35%, concentration $C_2$ at 25~45%, concentration $C_3$ at 35~55%, and concentrations $C_4$~$C_7$ at 40~60% each, a desired acrylamide concentration of 45~55% is achieved in the reaction mixture continuously retrieved from the seventh reaction vessel.

(8) Number of Reaction Vessels (N) is 8 or Greater

By setting concentration $C_1$ of the acrylamide solution contained in the first reaction vessel positioned on the furthest upstream side at 5~15%, and by setting the concentration in a downstream-side reaction vessel to be at least the same as but no greater than an addition of 10% to the concentration in the reaction vessel adjacent to it on the upstream side, a desired acrylamide concentration of 25~34% is achieved in the reaction mixture continuously retrieved from the reaction vessel positioned on the lowermost stream side.

Also, by setting concentration $C_1$ at 5~20%, and by setting the concentration in a downstream-side reaction vessel to be at least the same as but no greater than an addition of 10% to the concentration in the reaction vessel adjacent to it on the upstream side, a desired acrylamide concentration of 35~44% is achieved in the reaction mixture continuously retrieved from the reaction vessel positioned on the lowermost stream side.

Moreover, by setting concentration $C_1$ at 10~30%, and by setting the concentration in a downstream-side reaction vessel to be at least the same as but no greater than an addition of 10% to the concentration in the reaction vessel adjacent to it on the upstream side, a desired acrylamide concentration of 45~55% is achieved in the reaction mixture continuously retrieved from the reaction vessel positioned on the lowermost stream side.

The liquid amount of an acrylamide solution to be introduced in advance into a reaction vessel prior to initiating continuous reactions of the present invention is set at 70~120% of the liquid amount in the reaction vessel during continuous reactions. The liquid amount of an acrylamide solution is preferred to be 80~110%, more preferably 90~105%.

When the liquid amount of an acrylamide solution to be introduced is set at 70% or more, it will not take long from the start of continuous reactions until an acrylamide solution is retrieved. As a result, deterioration of a biocatalyst is prevented and the consumption amount of the biocatalyst will not increase. In addition, when the liquid amount of the acrylamide solution to be introduced is set at 120% or less, the retention time for the reaction liquid after the initiation of continuous reactions is prevented from being shortened to cause incomplete reactions. Accordingly, unreacted acrylonitrile will not be mixed into the produced acrylamide solution.

In the embodiment of the present invention, the amount of a biocatalyst to be introduced in a reaction vessel prior to initiating continuous reactions is set at 3000~150000 U (activity at reaction temperature of 10° C.) per 1 liter of the liquid in the reaction vessel. Here, the liquid in a reaction vessel indicates the acrylamide solution to be introduced in the reaction vessel prior to initiating continuous reactions. The time for introducing a biocatalyst may be before or after an acrylamide solution is introduced. However, to suppress deterioration of a biocatalyst, it is preferred to be after an acrylamide solution is introduced and shortly before the initiation of continuous reactions. By introducing a biocatalyst before initiating continuous reactions, an acute increase in the acrylonitrile concentration is prevented from occurring after continuous reactions have started, and the consumption amount of the biocatalyst is reduced. Moreover, reactions will reach a stable phase promptly.

Unless an increase in acrylonitrile concentration shortly after the initiation of continuous reactions is sufficiently suppressed, the biocatalyst deteriorates due to a high concentration of acrylonitrile; however, such deterioration can be prevented when the concentration of a biocatalyst to be introduced in a vessel is set at 3000 U/L or higher. As a result, an increase in the consumption amount of a biocatalyst is prevented, and the production cost of acrylamide is kept low.

On the other hand, when the concentration of a biocatalyst is set at 150,000 U/L or lower, impurities derived from the catalyst are prevented from being mixed into the produced acrylamide solution. As a result, adverse effects on the color tone of the acrylamide solution or on production of acrylamide polymers are prevented.

EXAMPLES

In the following, the present invention is described in detail with reference to examples and comparative examples. However, the present invention is not limited to the descriptions below. The concentration of acrylamide solutions may be simply described by using "%" instead of "mass %."

Example 1

(Preparation of Biocatalyst)

In a medium (pH 7.0) containing glucose at 2%, urea at 1%, peptone at 0.5%, yeast extract at 0.3% and cobalt chloride hexahydrate at 0.01% (percentages are all in mass %), *Rhodococcus rhodochrous* J1 having nitrile hydratase activity (internationally deposited on Sep. 18, 1987 as accession number "FERM BP-1478" with the International Patent Organism Depositary, the National Institute of Advanced Industrial Science and Technology at Chuo 6 1-1-1 Higashi, Tsukuba-shi, Ibaraki Prefecture, Japan) was cultured aerobically at 30° C. Cells were collected and washed by using a centrifuge and a 50 mM phosphate buffer (pH 7.0). Accordingly, a cell suspension (containing 15 mass % of dry cells) was obtained.

(Reactions to Produce Acrylamide from Acrylonitrile)

Six reaction vessels each having a 5-liter inner volume and a cooling jacket (inner diameter: 18 cm) attached to the vessel were connected in series. A mixer with four tilted paddle blades (tilted angle: 45 degrees, blade diameter: 8 cm) was provided in each reaction vessel. In the present embodiment, the target concentration of an acrylamide solution to be retrieved from a reaction vessel was set at 50~55% (the target concentration was set the same in Examples 2 and 3 and Comparative Examples 1 and 2).

(1) Valves of a channel connecting reaction vessels were closed.
(2) Four liters of acrylamide solutions with concentrations at 21%, 35%, 43%, 50%, 52% and 52% respectively were introduced into the first through sixth reaction vessels.
(3) The cell suspension prepared in Example 1 was added to each of the first through sixth reaction vessels in the amount to achieve 135,000 U of activity (at reaction temperature of 10° C.).
(4) Valves of the channel connecting each reaction vessel were opened.
(5) Continuous reactions were initiated by continuously supplying 50 mM phosphate buffer (pH 7.0) at 2146 g/hr, acrylonitrile at 569 g/hr and the cell suspension prepared in Example 1 at 8 g/hr into the first vessel; and in the second through fourth vessels, only acrylonitrile was supplied continuously at 380 g/hr, 292 g/hr, and 127 g/hr respectively.
(6) The overflow drainage port of the sixth vessel was adjusted so that the liquid amount of the reaction mixture in each reaction vessel was kept at 4 liters.

The temperatures of reaction liquids in the first through sixth vessels were controlled to be 20° C., 21° C., 22° C., 23° C., 24° C. and 25° C. respectively by using cooling water (5° C.) in the jackets.

Immediately after continuous reactions were initiated, the acrylamide concentration in the reaction liquid flowing out of the sixth vessel was analyzed using a refractometer (RX-7000α, made by Atago Co., Ltd.). A target acrylamide concentration of 52% was detected.

Five hours after the initiation of continuous reactions, the acrylamide concentration in the reaction liquid flowing out of the sixth vessel was analyzed. A target acrylamide concentration of 50% was detected.

Ten hours after the initiation of continuous reactions, the acrylamide concentration in the reaction liquid flowing out of the sixth vessel was analyzed. A target acrylamide concentration of 51% was detected.

Fifteen hours after the initiation of continuous reactions, the acrylamide concentration in the reaction liquid flowing out of the sixth vessel was analyzed. A target acrylamide concentration of 52% was detected.

Example 2

The same procedure as that in Example 1 was employed except that four liters of acrylamide solutions with concentrations at 32%, 43%, 50%, 50%, 52% and 52% respectively were introduced into first through sixth reaction vessels prior to the initiation of continuous reactions.

Immediately after continuous reactions were initiated, the acrylamide concentration in the reaction liquid flowing out of the sixth vessel was analyzed using the same method as in Example 1. A target acrylamide concentration of 52% was detected.

Five hours after the initiation of continuous reactions, the acrylamide concentration in the reaction liquid flowing out of the sixth vessel was analyzed. A target acrylamide concentration of 54% was detected.

Ten hours after the initiation of continuous reactions, the acrylamide concentration in the reaction liquid flowing out of the sixth vessel was analyzed. A target acrylamide concentration of 53% was detected.

Fifteen hours after the initiation of continuous reactions, the acrylamide concentration in the reaction liquid flowing out of the sixth vessel was analyzed. A target acrylamide concentration of 52% was detected.

Example 3

The same procedure as that in Example 1 was employed except that four liters of acrylamide solutions with concentrations at 15%, 27%, 37%, 40%, 40% and 40% respectively were introduced into the first through sixth reaction vessels prior to the initiation of continuous reactions.

Immediately after continuous reactions were initiated, the acrylamide concentration in the reaction liquid flowing out of the sixth vessel was analyzed using the same method as in Example 1. An acrylamide concentration of 40%, which was lower than the target concentration, was detected.

Five hours after the initiation of continuous reactions, the acrylamide concentration in the reaction liquid flowing out of the sixth vessel was analyzed. An acrylamide concentration of 48%, which was lower than the target concentration, was detected.

Ten hours after the initiation of continuous reactions, the acrylamide concentration in the reaction liquid flowing out of the sixth vessel was analyzed. A target acrylamide concentration of 51% was detected.

Fifteen hours after the initiation of continuous reactions, the acrylamide concentration in the reaction liquid flowing out of the sixth vessel was analyzed. A target acrylamide concentration of 52% was detected.

Comparative Example 1

The same procedure as that in Example 1 was employed except that four liters of water was introduced into each of the first through sixth reaction vessels prior to the initiation of continuous reactions.

Immediately after continuous reactions were initiated, the acrylamide concentration in the reaction liquid flowing out of the sixth vessel was analyzed using the same method as in Example 1. No acrylamide was detected.

Five hours after the initiation of continuous reactions, the acrylamide concentration in the reaction liquid flowing out of the sixth vessel was analyzed. An acrylamide concentration of 8%, which was lower than the target concentration, was detected.

Ten hours after the initiation of continuous reactions, the acrylamide concentration in the reaction liquid flowing out of the sixth vessel was analyzed. An acrylamide concentration of 42%, which was lower than the target concentration, was detected.

Fifteen hours after the initiation of continuous reactions, the acrylamide concentration in the reaction liquid flowing out of the sixth vessel was analyzed. An acrylamide concentration of 48%, which was lower than the target concentration, was detected.

Comparative Example 2

The same procedure as that in Example 1 was employed except that neither acrylamide solution nor raw water was introduced into the first through sixth reaction vessels prior to the initiation of continuous reactions.

Immediately after continuous reactions were initiated, no reaction liquid was flowed out of the sixth vessel. For some time after the initiation of continuous reactions, the liquid surface of the reaction mixture stayed lower than the mixer blades, and the raw water, biocatalyst and acrylonitrile supplied to reaction vessels were not well mixed.

Five hours after continuous reactions were initiated, no reaction liquid had flowed out of the sixth vessel. Ten hours after the initiation of continuous reactions, the acrylamide concentration in the reaction liquid flowing out of the sixth vessel was analyzed. An acrylamide concentration of 36%, which was lower than the target concentration, was detected.

Fifteen hours after continuous reactions were initiated, the acrylamide concentration in the reaction liquid flowing out of the sixth vessel was analyzed. An acrylamide concentration of 43%, which was lower than the target concentration, was detected.

<Concentration of Acrylamide Solution Introduced into Reaction Vessel Prior to Initiation of Continuous Reactions>

TABLE 1

| reaction vessel | 1 | 2 | 3 | 4 | 5 | 6 |
|---|---|---|---|---|---|---|
| Ci | 18 | 31 | 39 | 42 | 42 | 42 |
| example 1 | 21 | 35 | 43 | 50 | 52 | 52 |
| example 2 | 32 | 43 | 50 | 50 | 52 | 52 |
| example 3 | 15 | 27 | 37 | 40 | 40 | 40 |
| comp. example 1 | 0 | 0 | 0 | 0 | 0 | 0 |
| comp. example 2 | prior to initiating continuous reactions, no acrylamide solution or raw water was introduced | | | | | |

<Acrylamide Concentration in Reaction Liquid Flowed out from Sixth Vessel>

TABLE 2

| | time after initiating continuous reactions | | | |
|---|---|---|---|---|
| | 0 hr. | 5 hrs. | 10 hrs. | 15 hrs. |
| example 1 | 52% | 50% | 51% | 52% |
| example 2 | 52% | 54% | 53% | 52% |
| example 3 | 40% | 48% | 51% | 52% |
| comp. example 1 | 0% | 8% | 42% | 48% |
| comp. example 2 | no flow | no flow | 36% | 43% |

INDUSTRIAL APPLICABILITY

According to a method for continuously producing acrylamide by using a biocatalyst as described in the embodiment of the present invention, an acrylamide solution with a desired concentration level is continuously retrieved from shortly after the initiation of continuous reactions. As a result, a concentration or recovery procedure is simplified or unrequired, and acrylamide is produced at low cost with simplified procedures.

What is claimed is:

1. A method for producing acrylamide from acrylonitrile in the presence of a biocatalyst by a continuous reaction conducted in N number of reaction vessels that are connected in series, where N is a whole number of 2 or greater, the method comprising:
   initiating the continuous reaction by introducing acrylamide and optionally the biocatalyst into a first reaction vessel positioned on the furthest upstream side of the continuous reaction, and thereafter bringing the acrylonitrile and, if no biocatalyst is present in said first reaction vessel, the biocatalyst into contact with the acrylamide and any biocatalyst in the first reaction vessel wherein the biocatalyst converts the acrylonitrile into acrylamide in said N number of reaction vessels.

2. The method according to claim 1, wherein acrylamide is present in a reaction vessel into which an acrylonitrile solution is directly supplied.

3. The method according to claim 2, wherein N=2-10.

4. The method according to claim 1, wherein said biocatalyst is selected from animal cells, plant cells, organelles, live bacterial cells, and dead bacterial cells.

5. The method according to claim 4, wherein N=2-10.

6. The method according to claim 4, wherein said biocatalyst is selected from animal cells, plant cells, live bacterial cells, and dead bacterial cells, and wherein the activity of the biocatalyst is 50~500 U per 1 milligram of dry cells at a reaction temperature of 10° C. wherein a unit is the activity to produce 1 micromole/1 min of acrylamide from acrylonitrile.

7. The method according to claim 1, wherein the acrylonitrile has a hydrocyanic acid concentration of 3 ppm or lower.

8. The method according to claim 1, wherein N=2-10.

9. The method according to claim 1, comprising initiating the continuous reaction by introducing acrylamide and the biocatalyst into the first reaction vessel positioned on the furthest upstream side of the continuous reaction and thereafter bringing the acrylonitrile into contact with the acrylamide and the biocatalyst in the first reaction vessel.

10. The method according to claim 9, wherein N=2-10.

11. The method according to claim 9, further comprising adding said biocatalyst and said acrylamide to each of said N reaction vessels prior to said initiating the continuous reaction.

12. The method according to claim 11, wherein N=2-10.

13. The method according to claim 1, comprising initiating the continuous reaction by introducing acrylamide and no biocatalyst into the first reaction vessel positioned on the furthest upstream side of the reaction and thereafter bringing the acrylonitrile and the biocatalyst into contact with the acrylamide in the first reaction vessel.

14. The method according to claim 13, wherein N=2-10.

* * * * *